United States Patent [19]

Coviello

[11] Patent Number: 5,385,533

[45] Date of Patent: Jan. 31, 1995

[54] FAUCET ORAL JET RINSE

[76] Inventor: Michael P. Coviello, 315 E. Venetian Ct., Merritt Island, Fla. 32953

[21] Appl. No.: 61,294

[22] Filed: May 14, 1993

[51] Int. Cl.[6] ............................................. A61H 9/00
[52] U.S. Cl. ..................................... 601/165; 285/8; 239/428.5
[58] Field of Search ............................ 433/80; 128/66; 239/428.5; 285/8; 601/162, 163, 164, 165

[56] References Cited

U.S. PATENT DOCUMENTS

| | | | |
|---|---|---|---|
| 3,134,127 | 5/1964 | Klein | 15/321 |
| 3,208,145 | 9/1965 | Turner | 128/276 |
| 3,227,380 | 1/1966 | Pinkston | 285/8 |
| 3,771,517 | 11/1973 | Radecki | 128/66 |
| 4,108,167 | 8/1978 | Hickman et al. | 128/66 |
| 4,133,482 | 1/1979 | Moret | 128/66 |
| 4,135,501 | 1/1979 | Leunissan | 128/66 |
| 4,215,476 | 8/1980 | Armstrong | 433/80 |
| 4,302,186 | 11/1981 | Cammack et al. | 433/80 |
| 4,313,564 | 2/1982 | Shames et al. | 239/428.5 |
| 4,337,040 | 6/1982 | Cammack et al. | 433/80 |
| 4,397,640 | 8/1983 | Haug et al. | 604/33 |
| 4,808,109 | 2/1989 | Thornton | 433/216 |
| 4,941,459 | 7/1990 | Mathur | 128/66 |
| 4,942,870 | 7/1990 | Damien | 128/66 |
| 4,989,590 | 2/1991 | Baum et al. | 128/66 |

Primary Examiner—John J. Wilson

[57] ABSTRACT

A device for dislodging and removing matter from between and around teeth and gums through direct application of a high velocity jet of water and includes a quick disconnect coupling fitting (hereafter referred to as the "QD"), a sliding aerator, a quick disconnect plug fitting (hereafter referred to as the "plug"), a small diameter flexible tubing and a jet tip assembly. The QD replaces the standard lavatory faucet aerator. The lower end of the QD is shaped, slotted and grooved for connection to a mating plug. The plug is designed to insert and lock into the lower open end of the QD. A flexible tubing provides flow through capability and connects the plug to a jet tip assembly comprised of a handle and nozzle (jet tip). The plug, flexible tubing and jet tip assembly provide a temporary installation while the device is in use. When the device is not in use, a sliding aerator is restrained inside the QD at a lower position and functions as a normal aerator. Insertion and twisting of the plug into the bottom of the QD pushes the aerator upwards, and locks the plug into the QD. Manipulation of the hot and cold water taps controls water temperature and pressure. Removal of the plug allows the aerator to slide back down to the lower position and once again function as a normal aerator.

2 Claims, 7 Drawing Sheets

FAUCET ORAL JET RINSE

BRIEF SUMMARY OF THE INVENTION

The principal objects underlying the invention are to provide a safer, inexpensive, easier to operate oral jet rinse and teeth cleaning device for family use, which connects to a standard lavatory faucet utilizing direct continuous household faucet water and which appears and functions as a standard faucet aerator when not in use. Further objects are that the device be small, attractive, powerful, and quiet operating with the ability to regulate the wafer temperature and pressure.

The novel portion of the invention is the quick disconnect coupling assembly which appears and functions similar to that of a standard faucet aerator, but instead of containing a fixed aeration and flow restricting system, it is designed with a chamber which houses a "sliding aerator" and has provisions for single handed quick connect/quick disconnect features allowing positive connection and leak tight sealing with a corresponding male quick disconnect plug. Flexible tubing connects the quick disconnect plug to a jet tip assembly, where because of its elongated nozzle and tapered design, a high velocity jet of water is produced for cleaning teeth and massaging gums.

Once the quick disconnect coupling assembly is installed onto the lavatory faucet, the device is ready to use. The quick disconnect plug, flexible tubing and jet tip assembly comprise a temporary installation while the device is in use. When the device is not in use, the sliding aerator is restrained in a "lower" position inside the quick disconnect coupling by a mechanical stop, and in this position functions as a normal aerator (to restrict flow and mix air with the water to "soften" the water as it impacts the sink basin). Insertion of the quick disconnect plug into the bottom of the quick disconnect coupling "pushes" the sliding aerator upwards, exposing a containment groove for the quick disconnect plug restraint pins and a sealing surface for the quick disconnect plug resilient o-ring. Manipulation of the hot and cold water taps controls water temperature and pressure and provides a limitless supply of water for massaging and cleaning teeth and gums. Removal of the quick disconnect plug allows the sliding aerator to "slide" back down to the lower position and once again function as a normal aerator.

The present device is inherently safer than existing oral jet rinse devices due to its passive design. Potential for electric shock is eliminated though non-use of electric pumps or electrical devices. Extensive use of molded plastic parts, simplicity of design, and lack of electric pumps and other mechanisms, enables the present device to be produced and marketed a lower cost than prior art oral jet rinse devices.

The present device is easier to operate than convention oral jet rinses. Once installed, operations consist of connecting the quick disconnect plug to the quick disconnect coupling and turning on the faucet taps to produce a powerful jet of water. Because there are no moving parts or pumps to wear out, break, or make noise, the device is extremely quiet and will not disturb other members of the household during early morning or late evening hours. The requirement to repeatedly refill a water reservoir is eliminated due to the continuous water supply.

Since the device, in part, appears as a standard lavatory faucet aerator, its appearance is attractive and unobtrusive. The remaining portable portion of the device is also pleasant in appearance and is extremely small, lightweight and may be stored in any medicine cabinet, unlike bulky electrical jet rinses with water reservoirs.

Important features of this device include the ability to adjust water temperature and pressure of the jet stream. Though use of the hot and cold water taps, the water temperature and pressure may be regulated for personal comfort.

Other objects and features of advantage, together with the foregoing, are described in the following description and illustrated in the accompanying drawings.

BACKGROUND OF THE INVENTION

The present invention relates to an oral jet rinse and teeth cleaning device for family household purposes utilizing direct lavatory water pressure to produce a powerful jet of water to aid in the removal of food particles and debris from gums and teeth as part of a daily dental hygiene program.

Much attention has been given to the care and preservation of the teeth and gums, to substances used, and to various types of apparatus employing a jet of water for cleaning the teeth and massaging the gums. Such apparatus are old and well known in the arts and are generally characterized as being structurally complex, expensive to manufacture, and unsightly or inconvenient to use. The present device overcomes these shortcomings of the prior art.

One form of prior art of the invention is evidenced by U.S. Pat. No. 4,135,501 which employs a dental massage device that fits over and "grips" the exterior surface of a conventional faucet aerator in a sealing relationship therewith. A nozzle is connected to the device by means of a flexible conduit to eject water in a spray. Disadvantages known associated with this form of prior art include; 1) faucet aerators are not manufactured in one standard size, consequently, the "grip" design for the device may not fit and seal around all aerators, 2) the "grip" design is not a positive locking mechanism, but utilizes a "friction fit" method which may slip due the employment of water pressure, and 3) the o-ring used to provide a sealing surface is an unrestrained o-ring and may shift or dislodge during repeated insertion of the faucet aerator.

Another form of prior art of the invention is evidenced by U.S. Pat. No. 4,942,870 which is a dental hygiene device that also utilizes faucet water as a water source. It employs a fitting that replaces the faucet aerator and a connecting device that fits over and clamps to the fitting to utilize faucet water. A nozzle is connected to the device by means of a flexible conduit to eject water in a spray. The device also employs a pressure relief device to ensure the water pressure does not exceed a preset value. Disadvantages known associated with this form of prior art include; 1) the removable portion of the device is unsightly and cumbersome, 2) the fitting that replaces the faucet aerator is unsightly and does not resemble a conventional faucet aerator, 3) the fitting that replaces the faucet aerator is an "open" fitting and does not contain an aerator to aerate the water or to shape the water so that it flows in a formed and steady stream, and 4) the fitting that replaces the faucet aerator does not restrict the flow of water for water conservation.

Related prior art of the invention for providing pulsed jets of water which are directed against the teeth and gums for the purpose of cleaning the teeth and massaging the gums is evidenced by U.S. Pat. Nos. 4,108,167, 4,302,186, 4,337,040, and 4,989,590 which utilize an electric pump, refillable water reservoir and hand held nozzles. Certain disadvantages are known associated with this form of prior art. These include; 1) the use of electricity (especially in the presence of water) imposes inherent hazards of burns, electrocution and fire caused by operator error, damaged electrical cord or plug or damaged unit, 2) operation of the electric pumping system produces noise which may awaken or disturb sleeping family members during early morning or late evening hours, 3) limited capacity water reservoirs must be refilled as the water is spent (the operator must turn off the device, refill the reservoir with water, then turn the device back on to continue operations), 4) the use of moving parts in the device increases the chance of components/parts breakdown and repair, 5) the pumping system and reservoir is relatively bulky and consumes valuable counter space at lavatory sink counters, and 6) due to it's complexity, the cost of this form of prior art is expensive and not affordable to many households.

The present invention contains none of the disadvantages of the prior art. Through its simplicity of design and lack of moving parts of electricity, safety and convenience are increased, while noise, cost and maintenance is reduced. The specialized design of the quick disconnect coupling allows direct utilization of household faucet water pressure with the added benefits of limitless quantities of water, and controllable water temperature/pressure through adjustment of the hot and cold water taps.

BRIEF DESCRIPTION OF THE DRAWINGS

The novel features which I consider characteristic of my invention are set forth with particularity in the appended claims. The device itself, however, both as to its organization and mode of operation, together with additional objects and advantages thereof, will best be understood from the following description of specific embodiments when read in connection with the accompanying drawings, in which:

Synonymous reference numerals are employed throughout in the various views to refer to identical components.

FIG. 21-A, FIG. 21-B and FIG. 21-C show a sequence of three enlarged longitudinal sectional views of one form of a quick disconnect coupling assembly, quick disconnect plug and flexible tubing in accordance with the present invention and shown in operative association where:

FIG. 21-A quick disconnect plug is separate from quick disconnect coupling assembly and sliding aerator is resting in the "lower" position.

FIG. 21-B quick disconnect plug is partially inserted into quick disconnect coupling assembly, pushing sliding aerator upward and exposing locking grooves for restraint pins.

FIG. 21-C quick disconnect plug is fully inserted into quick disconnect coupling assembly and aerator is in the upper position.

While only the preferred form of the invention is illustrated in the drawings, it will be apparent that various modifications could be made without departing from ambit of the claims.

DESCRIPTION OF PREFERRED EMBODIMENT(S)

Figure 1:
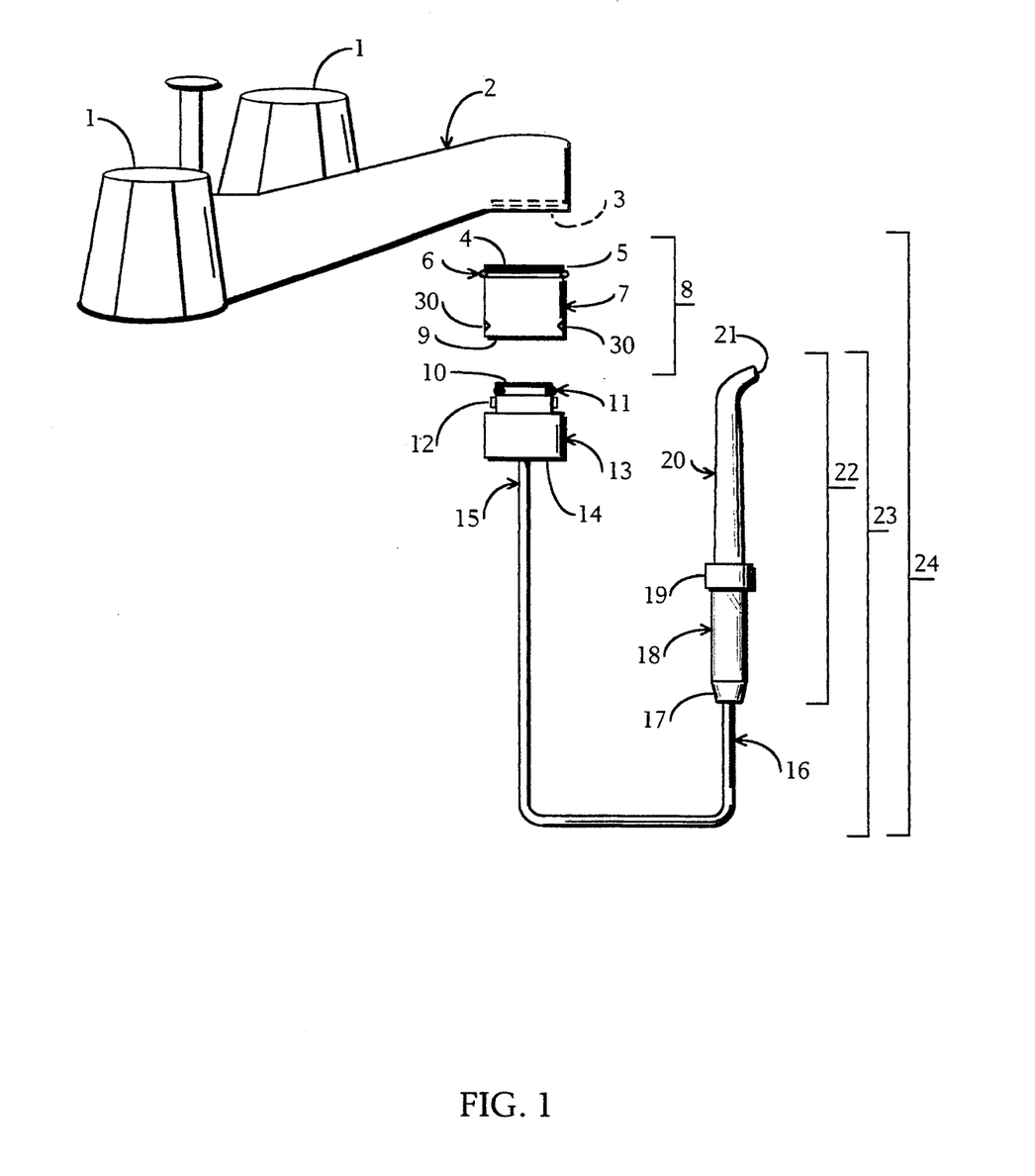
FIG. 1 is an assembled view of one form of a faucet oral jet rinse in accordance with the present invention and illustrated in operative association with the household lavatory water faucet.

FIG. 1 of the drawings illustrates the preferred form of the invention in the basic manner in which it is employed. Specifically, the present invention 24 is attached to lavatory faucet 2 in the manner described below, and upon control of hot and cold water taps 1 of lavatory faucet 2, water is caused to flow through quick disconnect coupling 7, quick disconnect plug 13 and flexible tubing 15/16 where it exits in a high velocity jet from tip 21 of nozzle 20. Water temperature and pressure is controlled through manipulation of hot and cold water taps 1. Tip 21 of nozzle 20 would then be placed between the teeth or along the gums and the stream of temperature/pressure regulated water allowed to squirt between the teeth and/or along the gums from both sides, whereby any food particles between the teeth and gums would be dislodged, while at the time massaging the gums. Such cleaning and treatment of the teeth and gums prevents infections, as well as cures infections and gum disease.

While quick disconnect coupling 7, quick disconnect plug 13, sliding aerator 25, flexible tubing 15/16, and jet tip assembly 22 of the present invention 24 is susceptible for numerous physical embodiments, those reflected in the drawings have been made, tested and used and all have performed in an eminently satisfactory manner.

Quick disconnect coupling 7 as illustrated in FIG. 3–FIG. 6 is a cylindrical shaped fitting having an appearance similar to that of a standard lavatory faucet aerator and contains features for allowing connection to a standard lavatory faucet 2, alignment and mating with corresponding quick disconnect plug 13, and containment of sliding aerator 25. The outer diameter of quick disconnect coupling 7 at upper end 4 is sized to commensurate with machining requirements for external machine threads 5 to mate with internal machine threads 3 of standard lavatory faucet 2. The outer diameter of main body 28 is the minimum required to accommodate sliding aerator 25 and containment groove 35 while maintaining structural integrity. The longitudinal length of quick disconnect 7 is the minimum required to allow full engagement of the mating quick disconnect plug 13, and movement of sliding aerator 25 (ref FIG. 21), while installed with threaded engagement to internal machine threads 3 of lavatory faucet 2. Thickness of quick disconnect coupling 7 is the minimum required for containment of pressurized water, threaded machining requirements, and containment of siding aerator 25, while providing a rigid structure for mating with the corresponding quick disconnect plug 13.

The upper end 4 of quick disconnect coupling 7 contains external machine threads 5 to mate with internal machine threads 3 of lavatory faucet 2 (optional internal threads may be machined into upper end 4 to allow for installation of screw type adapters for use with nonstandard faucets). Located immediately below external machine threads 5 is external groove 31 for containment of resilient o-ring 6 to provide a water tight seal with lavatory faucet 2 internal machine threads 3. Lower end 9 of quick disconnect coupling 7 contains two diamond shaped alignment marks 30 stamped into the external surface, located 180 degrees from one another on opposing sides of quick disconnect coupling 7. Alignment marks 30 indicate the location of key way slots 37 located on the bottom side of quick disconnect coupling 7.

Figure 19:
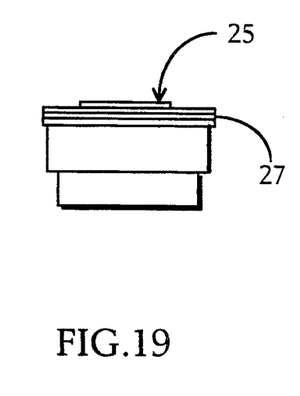
FIG. 19 is an enlarged side-elevational view of one form of a sliding aerator in accordance with the present invention.

Upper end 4 of quick disconnect coupling 7 is provided with a centrally located hole or aperture 32, the diameter of which is slightly greater than rim 27 of sliding aerator 25 (ref FIG. 19). This diameter provides adequate clearance for movement of sliding aerator 25. Approximately halfway down quick disconnect coupling 7, at location 33, the hole size decreases creating a new aperture 34 with a diameter sized to provide sufficient compression and sealing ability for resilient o-ring 11, as to provide a leak tight seal when resilient o-ring 11 is installed onto quick disconnect plug 13 and said plug installed into lower end 9 of quick disconnect coupling 7. Location 33 also serves as a mechanical stop to restrain rim 27 of sliding aerator 25. Within in aperture 34 is containment groove 35 for containment of quick disconnect plug 13 restraint pins 12 when said plug is installed into said coupling. Containment groove 35 is of sufficient depth and width as to accommodate restraint pins 12 with adequate clearance for insertion and removal of said pins. Containment groove 35 also contains two mechanical stops 36 located 180 degrees from one another on opposing sides of said groove and 90 degrees from position of key way slots 37. These mechanical stops 36 provide a barrier for restraint pins 12 when said pins are inserted and rotated within containment groove 35. Lower end 9 of quick disconnect coupling 7 also contains two machined key way slots 37 located 180 degrees from one another on opposing sides of quick disconnect coupling 7. Key way slots 37 provide passage way to containment groove 35 for restraint pins 12 of quick disconnect plug 13 when said plug is inserted into said coupling. The width of key way slots 37 is slightly greater than that of corresponding restraint pins 12.

Quick disconnect plug 13 as illustrated in FIG. 7–FIG. 10 is the mating half of the aforementioned quick disconnect coupling 7 and contains features for connecting with, sealing with and providing flow through capability with quick disconnect coupling 7 and flexible tubing 15/16, restraint pins 12 for locking quick disconnect plug 13 into quick disconnect coupling 7, grip 38 for holding and inserting said plug into said coupling, and alignment grooves 43 for visual positioning of quick disconnect plug 13 restraint pins 12 with corresponding key way slots 37 of quick disconnect coupling 7. Quick disconnect plug 13 is irregular in shape and contains various protruding flanges and appendages for performing various functions. Grip 38 of quick disconnect plug 13 has an outer diameter equaling that of the aforementioned quick disconnect coupling 7, so when the two are mated together, they appear cylindrical in shape.

Upper end 10 of quick disconnect plug 13 contains leading flange 39 which serves as one side of containment groove 40 for resilient o-ring 11 as well as providing a rigid leading surface for upper end 10 to "push" against sliding aerator 25 when quick disconnect plug 13 is inserted into quick disconnect coupling 7. Leading flange 39 has an outer diameter just slightly less than corresponding aperture 34 of quick disconnect coupling 7, while sufficiently large and thick enough as to provide a rigid structure for containment of resilient o-ring 11 when installed in containment groove 40 of quick disconnect plug 13.

Adjacent to leading flange 39 of quick disconnect plug 13 is containment groove 40 for containing resilient o-ring 11. The diameter of containment groove 40 is sized appropriately large as to provide sufficient compression and sealing ability for resilient o-ring 11 and provide a water tight seal with corresponding aperture 34 of quick disconnect coupling 13.

Adjacent to containment groove 40 of quick disconnect plug 13 is cylindrical surface 41 which serves as a spacer for positioning containment groove 40 well within aperture 34 of quick disconnect coupling 7 when said plug is inserted into said coupling. The outer diameter of cylindrical surface 41 is similar to that of the aforementioned leading flange 39 of quick disconnect plug 13.

Protruding from opposing sides of cylindrical surface 41 of quick disconnect plug 13, located 180 degrees from one another are two irregular shaped flanges which serve as restraint pins 12 for locking quick disconnect plug 13 to quick disconnect coupling 7 when they are mated. Restraint pins 12 are of generally triangular shape and are connected at their base to cylindrical surface 41. The height and width of restraint pins 12 are such that when said pins are inserted through key way slots 37 and twisted within containment groove 35 of quick disconnect coupling 7, adequate clearance is provided for free movement of said pins.

Adjacent to cylindrical surface 41 of quick disconnect plug 13 is grip 38 for providing a hand hold and for containing alignment grooves 43 used when inserting and removing quick disconnect plug 13 from quick disconnect coupling 7. The external surface of grip 38 is knurled to provide slip free handling of the device when wet. Grip 38 also contains two longitudinal alignment grooves 43 cut into the external surface, located 180 degrees from one another on opposing sides of said grip. Alignment grooves 43 mark the location of restraint pins 12 and are used in operative association with alignment marks 30 of quick disconnect coupling 7.

Figure 12:
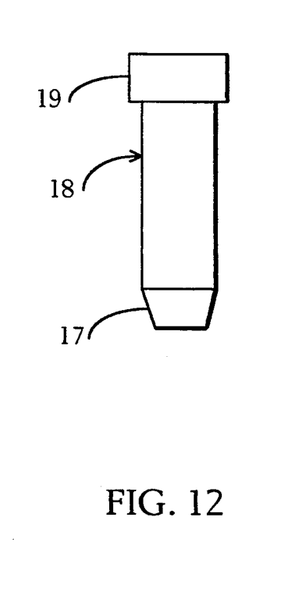
FIG. 12 is an enlarged longitudinal view of one form of a jet tip handle in accordance with the present invention.
Figure 14:
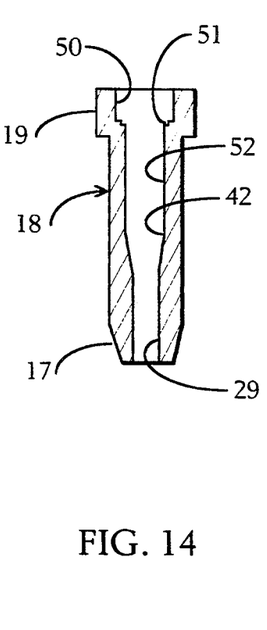
FIG. 14 is an enlarged longitudinal sectional view of one form of a jet tip handle in accordance with the present invention.
Figure 16:
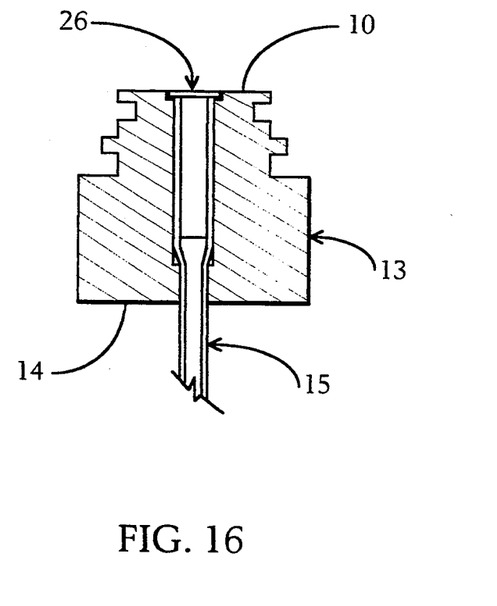
FIG. 16 is an enlarged longitudinal sectional view of one form of a quick disconnect plug shown in operative association with installed flexible tubing and insert in accordance with the present invention.

Upper end 10 of quick disconnect plug 13 is provided with a centrally located hole or aperture 44, the diameter of which is slightly greater than the outer diameter of insert 26. This diameter allows for compression of flexible tubing 15 and provides a tight fit and watertight seal when flexible tubing 15 and insert 26 are installed into aperture 44 (ref FIG. 16). The upper end of aperture 44 is enlarged to create recess 45 for flush installation of insert 26. At the lower end of aperture 44, at location 47, the hole size decreases creating a new aperture 46 with a diameter sized to provide a snug fit for flexible tubing 15 when installed through lower end 14 of quick disconnect plug 13. Jet tip handle 18 as illustrated in FIG. 12 and FIG. 14 is the handle portion of jet tip assembly 22 (ref FIG. 15) and contains features for connecting with, sealing with and providing flow through capability with nozzle 20 and flexible tubing 16.

Jet tip handle 18 is generally cylindrical in shape. The exterior surface of the main cylinder is knurled to provide slip free handling when wet. Lower end 17 of jet tip handle 18 is tapered for aesthetic purposes.

Upper end 19 of jet tip handle 18 has an enlarged cylindrical shape and is provided with a centrally located aperture 50 with a diameter slightly larger than that of mating lower end 48 of nozzle 20.

Adjacent to aperture 50 is recess 51 to allow flush installation of insert 26 when said insert in installed in jet tip handle 18. Recess 51 also provides a mechanical stop for installation of nozzle 20 into aperture 50. Located immediately beneath recess 51 is aperture 52, the diameter of which is slightly greater than the outer diameter of insert 26. This diameter allows compression of flexible tubing 16 and provides a tight fit and leak tight seal when flexible tubing 16 and insert 26 are installed into aperture 52. Approximately half way down jet tip handle 18 at location 42 the hole size decreases creating a new aperture 29 with a diameter sized to provide a snug fit for flexible tubing 16 when installed through lower end 17 of jet tip handle 18.

Figures 11, 13:
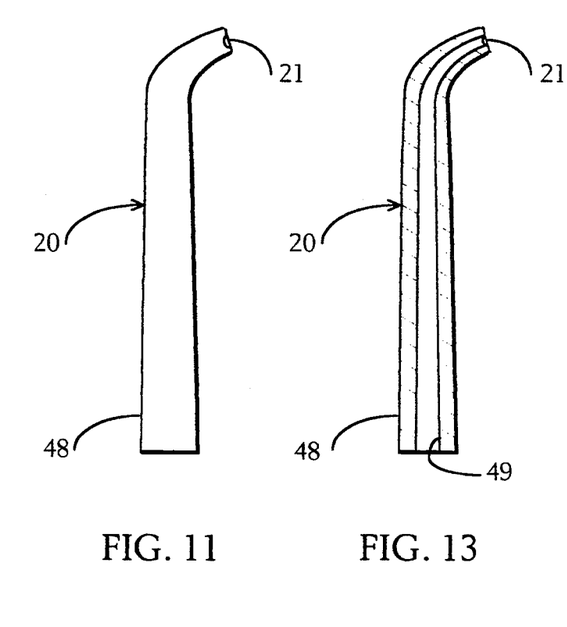
FIG. 11 is an enlarged longitudinal view of one form of a nozzle in accordance with the present invention.
FIG. 13 is an enlarged longitudinal sectional view of one form of a nozzle in accordance with the present invention.

Nozzle 20 as illustrated in FIG. 11 and FIG. 13 comprises a smooth elongated nozzle or ejector which increases the velocity of water and ejects the water in a jet stream from tip 21. The upper end of nozzle 20 is angled to provide the user with the ability to manipulate and direct the jet of water as desired.

Figure 21:
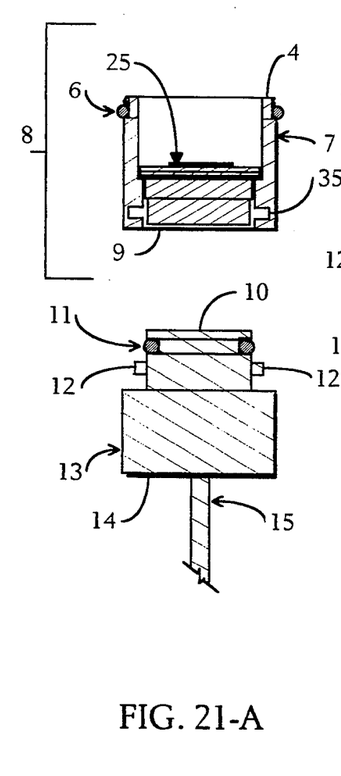

Lower end 48 of nozzle 20 is provided with a centrally located hole or aperture 49. The diameter of aperture 49 gently decreases along nozzle 20, thereby providing the nozzle effect which increases the velocity of the water. Aperture 49 terminates at tip 21 where the water is forcibly ejected creating a free spraying powerful jet of water. Quick disconnect coupling assembly 8 as illustrated in FIG. 1, FIG. 2 and FIG. 21 is an assembly of quick disconnect coupling 7, sliding aerator 25, and resilient o-ring 6 and is that portion of the present invention 24 that permanently replaces the lavatory faucet aerator 2.

Figure 15:
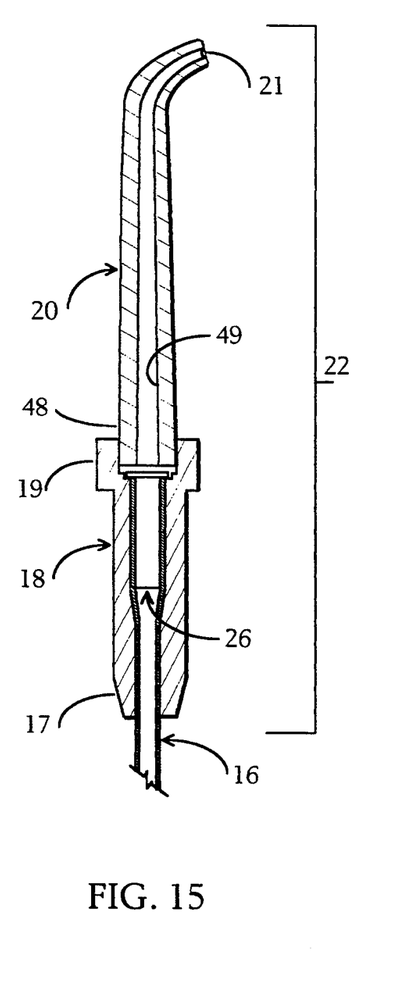
FIG. 15 is an enlarged longitudinal sectional view of one form of a jet tip assembly in accordance with the present invention.

Jet tip assembly 22 as illustrated in FIG. 15 is a combination of nozzle 20, jet tip handle 18, insert 26, and flexible tubing 16. Said assembly provides the user with the hand held operative portion of the present invention 24.

Installation of jet tip assembly 22 consists of inserting flexible tubing 16 through aperture 29 of lower end 17 of jet tip handle 18 such that flexible tubing 16 protrudes through aperture 50 of upper end 19 and installs over the barrel of insert 26. Combined insert 26 and said tubing is then forcibly positioned into aperture 50 and aperture 52 until the flange of insert 26 rests flush within recess 51. Lower end 48 of nozzle 20 is then installed within aperture 50 in a friction fit relationship. A permanent bond and leak tight seal of lower end 48 and aperture 50 is achieved through use of appropriate adhesive or sealing compound.

Figure 2:
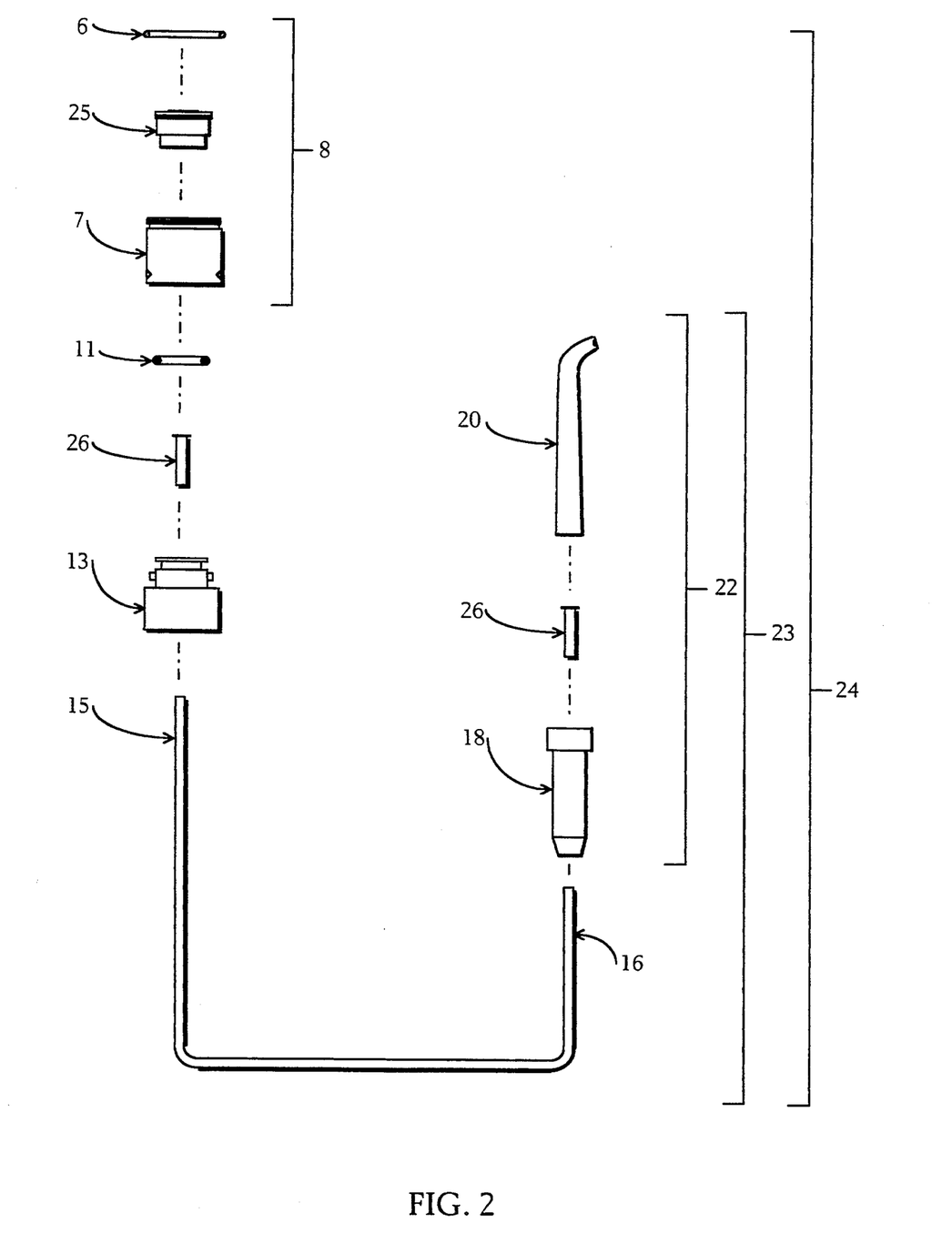
FIG. 2 is an exploded fragmentary view of one form of a faucet oral jet rinse in accordance with the prevent invention.
Figure 3:
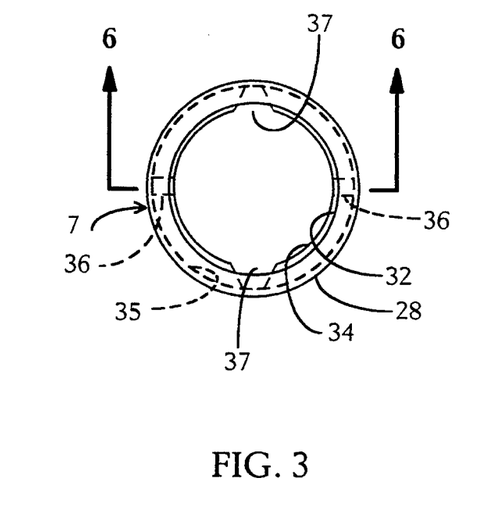
FIG. 3 is an enlarged plan view of one form of a quick disconnect coupling in accordance with the present invention.
Figure 4:
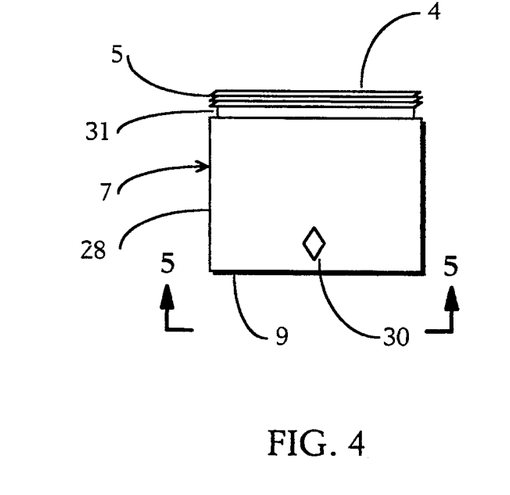
FIG. 4 is an enlarged front-elevational view of one form of a quick diconnect coupling in accordance with the present invention.
Figure 5:
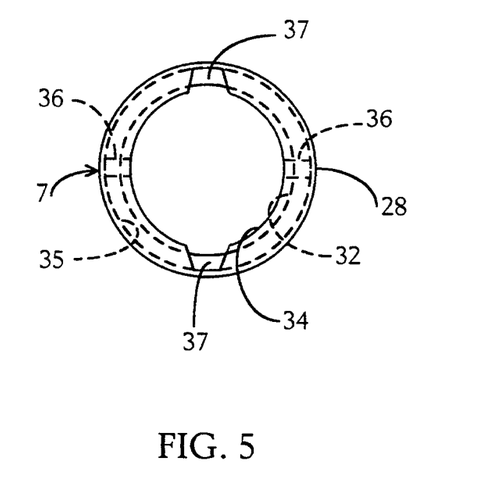
FIG. 5 is a bottom view of FIG. 4 quick disconnect coupling taken along line 5—5 in FIG. 4 from view 5—5.
Figure 6:
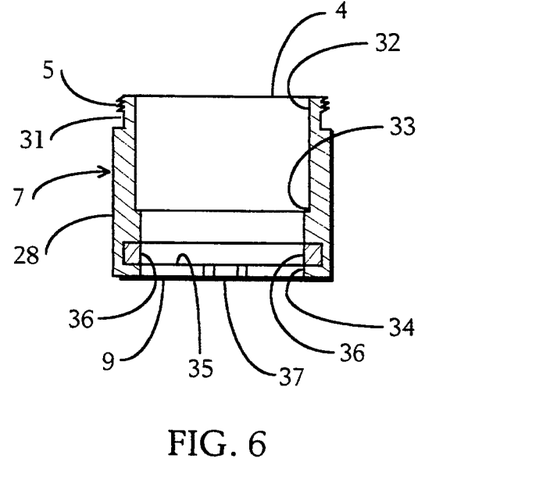
FIG. 6 is cross sectional view of FIG. 3 quick disconnect coupling taken along line 6—6 in FIG. 3.
Figure 7:
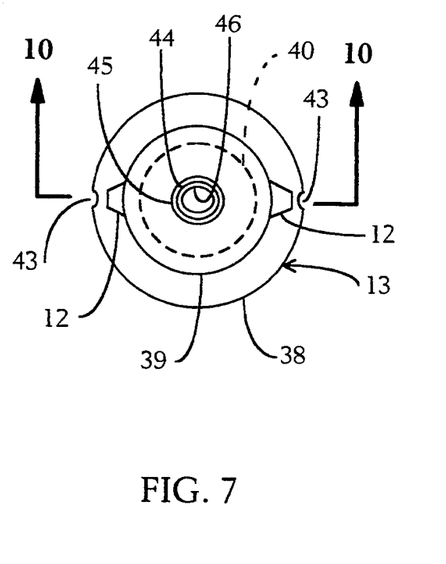
FIG. 7 is an enlarged plan view of one form of a quick disconnect plug in accordance with the present invention.
Figure 8:
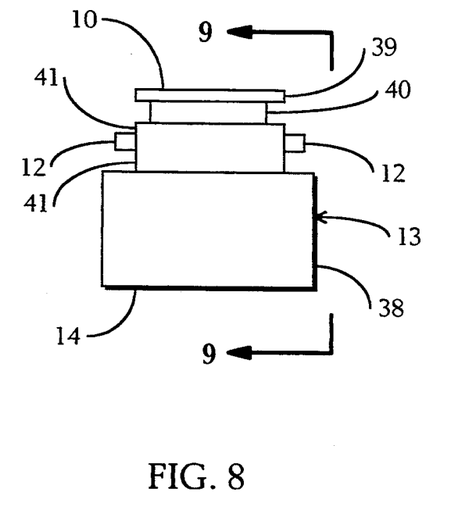
FIG. 8 is an enlarged front-elevational view of one form of a quick disconnect plug in accordance with the present invention.
Figure 9:
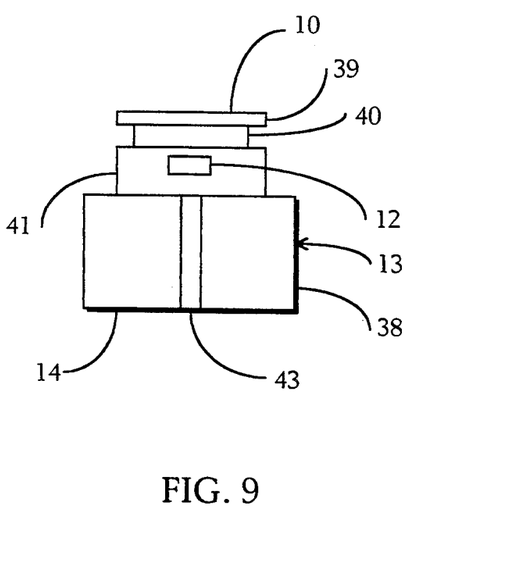
FIG. 9 is side-elevational view of FIG. 8 quick disconnect plug taken from view along line 9—9 in FIG. 8.
Figure 10:
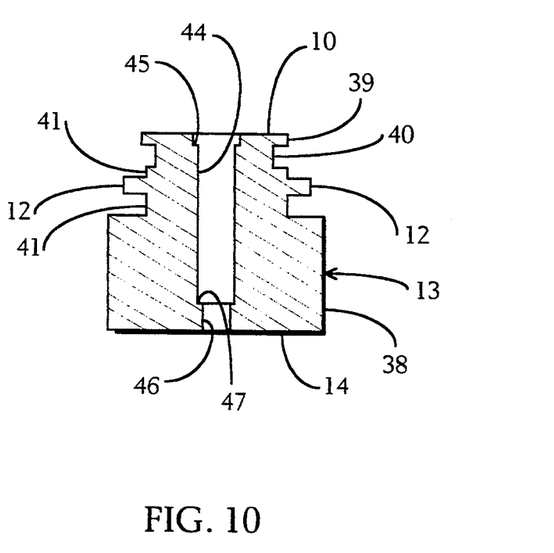
FIG. 10 is a cross sectional view of FIG. 7 taken along line 10—10 in FIG. 7.

Portable assembly 23 as illustrated in FIG. 1 and FIG. 2 is an assembly of quick disconnect plug 13, flexible tubing 15/16, insert 26, and jet tip assembly 22 and is the detachable and storable portion of present invention 24.

Sliding aerator 25 as illustrated in FIG. 19 is a composition of commercially available products assembled in a generally cylindrical form and functions to mix air with water as to "soften" the water to prevent splash as it impacts the lavatory basin. Said aerator also restricts water flow and "shapes" the stream of water as it flows from the faucet. Rim 27 of aerator 25 contains an enlarged diameter slightly greater than that of aperture 34 of quick disconnect coupling 7 and serves to contain said aerator in said coupling.

Figure 17:
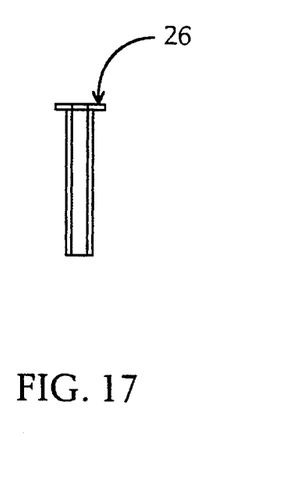
FIG. 17 is an enlarged longitudinal sectional view of one form of an insert in accordance with the present invention.
Figure 18:
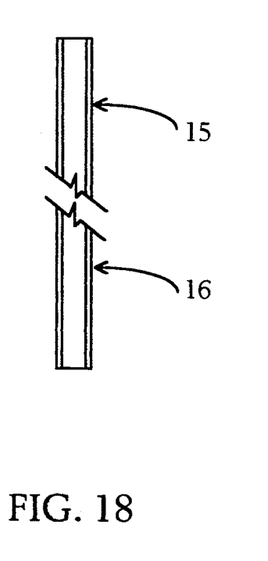
FIG. 18 is an enlarged longitudinal sectional view of one form of a flexible tubing in accordance with the present invention.
Figure 20:
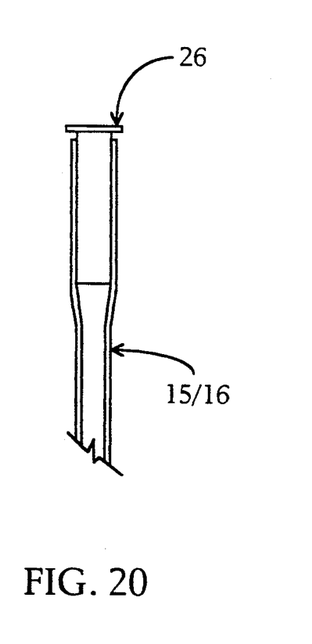
FIG. 20 is an enlarged longitudinal sectional view of one form of an insert shown in operative association when installed in flexible tubing in accordance with the present invention.

Insert 26 as illustrated in FIG. 17 and again in operative association with flexible tubing 15/16 in FIG. 20 is a rigid thin walled metallic conventional device available in the market today for use in various plumbing applications. Flexible tubing 15/16 (ref FIG. 18), resilient o-ring 6, and resilient o-ring 11 are also commercially available products in todays market.

Although the present invention 24 is illustrated and described in operative association with standard lavatory faucets, it is to be appreciated that said invention may be similarly employed in operative association with kitchen faucets, utility faucets and the like.

It will be apparent to one skilled in the art that various changes and modifications may be made in the invention without departing from its true scope and spirit. For example, the materials of construction can vary considerably. However, to achieve durability in operation while at the same time effecting a maximum of manufacturing economy, attention has been given to the formation of as many components as possible from plastic materials. Suitable materials for the quick disconnect coupling 7, quick disconnect plug 13, jet tip handle 18, and nozzle 20 would be nylon, polyvinyl chloride, and the like. Flexible tubing 15/16 can be made out of any suitable resilient material, such as various different rubbers, vinyl compounds and the like.

It is also intended that within the scope of the present invention 24, that quick disconnect coupling 7 itself, can be employed in a wide variety of implementations, for example to connect with a variety of unique quick disconnect plugs 13 for applications other than oral hygiene. One such plug may employ an eductor for aspiration purposes, another may contain an impeller to transform water pressure/flow into mechanical rotary motion for use multiple purposes.

From the foregoing, it will be seen that the oral jet rinse and teeth cleaning device of the present invention through an alternate concept of a water delivery system removes all of the disadvantages associated with the prior art, yet still provides effective food particle and debris removal capability.

In accordance with the provisions of the patent statue, the principles and modes of operations of the present invention have been illustrated and described in what is now considered the best embodiments of the invention. However, it is understood that the invention may be practiced otherwise than as specifically illustrated in the drawings and described in the specification without departing from its spirit of scope.

What I claim as invention is:

1. A fluid delivery system that connects to a faucet and functions as an aerator mechanism and as an oral hygiene system, comprising:
    a quick disconnect coupling having a cylindrical appearance similar to that of standard faucet aerators and means for threaded connection to faucets; flow through capability; containment and operation of a sliding aerator; aligning with, coupling with, sealing with and locking with a corresponding quick disconnect plug;
    a sliding aerator mechanism having a generally cylindrical appearance and means for flow through aeration of fluid and sliding action within the main chamber of said quick disconnect coupling;
    a quick disconnect plug having a generally cylindrical appearance and means for aligning with, coupling with, sealing with, and locking with the aforementioned quick disconnect coupling; and means for flow through capability, leak tight connection to a flexible hose, and single handed operations;
    a handle having a generally cylindrical appearance and means for fluid transfer and leak tight connection to a flexible hose and nozzle;
    a flexible hose having a smooth bore and means for fluid transfer and leak tight connection to the aforementioned quick disconnect plug and handle;
    a nozzle having a slender and tapered tubular appearance and an angled tip and means for connecting with and sealing with the aforementioned handle providing a leak tight seal and flow through capability;
    an insert having an annular passage and means for connecting with and sealing with said flexible hose;
    a means for sealing the aforementioned quick disconnect coupling and a faucet in a leak tight relationship therewith;
    a means for sealing the aforementioned quick disconnect coupling and the quick disconnect plug in a leak tight relationship therewith.

2. A quick disconnect coupling system that functions as a sliding aerator mechanism and as a fluid dispensing system, comprising:
    a quick disconnect coupling, having a cylindrical shape, and further including means for threaded connection to a faucet and means for allowing fluid to flow through said coupling, said flow through means includes a main chamber,
    a sliding aerator having a generally cylindrical shape and means for allowing fluid to flow through, said aerator being slidably located within said main chamber of said quick disconnect coupling,
    a quick disconnect plug having a generally cylindrical shape and including means for aligning with, coupling with and locking with said quick disconnect coupling, means for allowing fluid to flow through and means for single handed operations, said quick disconnect plug being removable coupled to said quick disconnect coupling,
    means for sealing said quick disconnect coupling to a faucet in a leak tight relationship,
    said quick disconnect coupling having means for sealing said coupling with said quick disconnect plug in a leak tight relationship,
    whereby, when said plug is not attached to said coupling, said aerator covers said coupling sealing means and when said plug is connected to said coupling, said aerator slides to uncover said coupling sealing means.

* * * * *